United States Patent
Hoskins et al.

(10) Patent No.: US 6,268,175 B1
(45) Date of Patent: Jul. 31, 2001

(54) STREPTOCOCCUS PNEUMONIAE GENE SEQUENCE GCP

(75) Inventors: Jo Ann Hoskins, Indianapolis; Joseph Chiou-Chung Tang, Carmel; Patti Jean Treadway, Greenwood, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/987,121

(22) Filed: Dec. 8, 1997

Related U.S. Application Data

(60) Provisional application No. 60/036,281, filed on Dec. 13, 1996.

(51) Int. Cl.$^7$ .............................. C07H 21/04; C12N 1/20; C12N 15/00; C12N 15/63
(52) U.S. Cl. ................... 435/69.1; 435/71.1; 435/252.3; 435/320.1; 435/471; 536/23.7
(58) Field of Search ................................ 435/69.1, 320.1, 435/252.3, 471, 71.1; 536/23.7; 530/350

(56) References Cited

U.S. PATENT DOCUMENTS

| | | | |
|---|---|---|---|
| 5,543,312 | * | 8/1996 | Mellors et al. ................... 435/220 |
| 5,591,839 | * | 1/1997 | Miller et al. ................... 536/23.7 |

OTHER PUBLICATIONS

USB Catalog. Molecular Biology Reagents, pp. 163–165, 1990.*

Saiz et al. Yeast. 12:1077–1084, 1996.*

Miriam D. Potter and Reggie Y.C. Lo. "Cloning and characterization of a gene from *Pasteurell haemolytica* A1 involved in lipopolysaccharide biosynthesis" *FEMS Microbiology Letters* 129:75–82 (1995).

Chiang W. Lee, et al. "The detection of the sialoglycoprotease gene and assay for sialoglycoprotease activity among isolates of *Pasteurella haemolytica* A1 strains, serotypes A13, A14, T15, and A16" *FEMS Microbiology Letters* 121:199–206 (1994).

Khalid M. Abdullah, et al. "Cloning, Nucleotide Sequence, and Expression of the *Pasteurella haemolytica* A1 Glycoprotease Gene" *Journal of Bacteriology* 173(18):5597–5603 (Sep. 1991).

Khalid M. Abdullah et al. "A Neutral Glycoprotease of *Pasteurella haemolytica* A1 Specifically Cleaves O–Sialoglycoproteins" *Infection and Immunity* 60(1) :56–62 (Jan. 1992).

Khalid M. Abdullah, et al. "Cloning Nucleotide Sequence, and Expression of the *Pasteurella haemolytica* A1 Glycoprotease Gene" *Journal of Bacteriology* 173(18):5597–5603 (Sep. 1991).

Alan Mellors and Reggie Y.C. Lo. "O–Sialoglycoprotease from *Pasteurella haemolytica*" *Methods in Enzymology* 248:728–741 (1995).

n–geneseq sequence printout. Accession No. A33358.* a–geneseq sequence printout. Accession No. R26325.*

* cited by examiner

Primary Examiner—Carla J. Myers
(74) Attorney, Agent, or Firm—Raymond S. Parker, III; Thomas D. Webster

(57) ABSTRACT

The invention provides isolated nucleic acid compounds encoding gcp of *Streptococcus pneumoniae*. Also provided are vectors and transformed host cells for expressing the encoded protein, and a method for identifying compounds that bind and/or inhibit said protein.

10 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 900 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
TGTCCCAAGA CCAGACTTGG TATGCTCTGG CCTATGATGG GGCAGAAGTG ATTGGCTTTC      60

TAACTGTTCA GGAGACTCTC TTTGAAGCAG AAGTCCTGCA AATCGCTGTC AAAGGAGCTT     120

ATCAGGGTCA GGGAATTGCG TCAGCCTTGT TTGCTCAATT GCCGACAGAC AAGGAAATTT     180
```

-continued

```
TCCTCGAAGT CAGACAGTCA AATCAACGAG CGCAAGCATT TTACAAGAAA GAAAAGATGG    240

CAGTTATCGC TGAGCGAAAG GCCTACTACC ATGACCCAGT CGAGGACGCC ATTATCATGA    300

AGAGAGAAAT AGATGAAGGA TAGATATATT TTAGCATTTG AGACATCCTG TGATGAGACC    360

AGTGTCGCCG TCTTGAAAAA CGACGATGAG CTCTTGTCCA ATGTCATTGC TAGTCAAATT    420

GAGAGTCACA AACGTTTTGG TGGCGTAGTG CCCGAAGTAG CCAGTCGTCA CCATGTCGAG    480

GTCATTACAG CCTGTATCGA GGAGGCATTG GCAGAAGCAG GGATTACCGA AGAGGACGTG    540

ACAGCTGTTG CGGTTACCTA CGGACCAGGC TTGGTCGGAG CCTTGCTAGT TGGTTTGTCA    600

GCTGCCAAGG CCTTTGCTTG GGCTCACGGA CTTCCACTGA TTCCTGTTAA TCACATGGCT    660

GGGCACCTCA TGGCAGCTCA GAGTGTGGAG CCTTTTGGAG TTTCCCTTGC TAGCCCTTTT    720

AGTTCAGTGG GTGGGGCACA CAGAGTTGGT CTATGTTTCT GAGGCTGGCG ATTACAAGAA    780

TTGTTGGGGA AGACACGAGA CGATGCAGTT GGGGAGGCTT ATGACAAGGT CGGTCGTGTC    840

ATGGCTTGAC CTATCCTGCA GGTCGTGAGA TTGACGAGCT GGCTCATCAG GGGCAGGATA    900
```

(2) INFORMATION FOR SEQ ID NO:2:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:2:

```
UGUCCCAAGA CCAGACUUGG UAUGCUCUGG CCUAUGAUGG GGCAGAAGUG AUUGGCUUUC     60

UAACUGUUCA GGAGACUCUC UUUGAAGCAG AAGUCCUGCA AAUCGCUGUC AAAGGAGCUU    120

AUCAGGGUCA GGGAAUUGCG UCAGCCUUGU UUGCUCAAUU GCCGCACAGAC AAGGAAAUUU    180

UCCUCGAAGU CAGACAGUCA AAUCAACGAG CGCAAGCAUU UUACAAGAAA GAAAAGAUGG    240

CAGUUAUCGC UGAGCGAAAG GCCUACUACC AUGACCCAGU CGAGGACGCC AUUAUCAUGA    300

AGAGAGAAAU AGAUGAAGGA UAGAUAUAUU UUAGCAUUUG AGACAUCCUG UGAUGAGACC    360

AGUGUCGCCG UCUUGAAAAA CGACGAUGAG CUCUUGUCCA AUGUCAUUGC UAGUCAAAUU    420

GAGAGUCACA AACGUUUUGG UGGCGUAGUG CCCGAAGUAG CCAGUCGUCA CCAUGUCGAG    480

GUCAUUACAG CCUGUAUCGA GGAGGCAUUG GCAGAAGCAG GGAUUACCGA AGAGGACGUG    540

ACAGCUGUUG CGGUUACCUA CGGACCAGGC UUGGUCGGAG CCUUGCUAGU UGGUUUGUCA    600

GCUGCCAAGG CCUUUGCUUG GGCUCACGGA CUUCCACUGA UUCCUGUUAA UCACAUGGCU    660

GGGCACCUCA UGGCAGCUCA GAGUGUGGAG CCUUUUGGAG UUUCCCUUGC UAGCCCUUUU    720

AGUUCAGUGG GUGGGGCACA CAGAGUUGGU CUAUGUUUCU GAGGCUGGCG AUUACAAGAA    780

UUGUUGGGGA AGACACGAGA CGAUGCAGUU GGGGAGGCUU AUGACAAGGU CGGUCGUGUC    840

AUGGCUUGAC CUAUCCUGCA GGUCGUGAGA UUGACGAGCU GGCUCAUCAG GGGCAGGAUA    900
```

(2) INFORMATION FOR SEQ ID NO:3:

(i) SEQUENCE CHARACTERISTICS:
        (A) LENGTH: 1011 base pairs
        (B) TYPE: nucleic acid
        (C) STRANDEDNESS: single
        (D) TOPOLOGY: linear -continued (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 1..1008

(xi) SEQUENCE DESCRIPTION: SEQ ID NO:3:

```
ATG AAG GAT AGA TAT ATT TTA GCA TTT GAG ACA TCC TGT GAT GAG ACC        48
Met Lys Asp Arg Tyr Ile Leu Ala Phe Glu Thr Ser Cys Asp Glu Thr
 1               5                  10                  15

AGT GTC GCC GTC TTG AAA AAC GAC GAT GAG CTC TTG TCC AAT GTC ATT        96
Ser Val Ala Val Leu Lys Asn Asp Asp Glu Leu Leu Ser Asn Val Ile
             20                  25                  30

GCT AGT CAA ATT GAG AGT CAC AAA CGT TTT GGT GGC GTA GTG CCC GAA       144
Ala Ser Gln Ile Glu Ser His Lys Arg Phe Gly Gly Val Val Pro Glu
         35                  40                  45

GTA GCC AGT CGT CAC CAT GTC GAG GTC ATT ACA GCC TGT ATC GAG GAG       192
Val Ala Ser Arg His His Val Glu Val Ile Thr Ala Cys Ile Glu Glu
 50                  55                  60

GCA TTG GCA GAA GCA GGG ATT ACC GAA GAG GAC GTG ACA GCT GTT GCG       240
Ala Leu Ala Glu Ala Gly Ile Thr Glu Glu Asp Val Thr Ala Val Ala
 65                  70                  75                  80

GTT ACC TAC GGA CCA GGC TTG GTC GGA GCC TTG CTA GTT GGT TTG TCA       288
Val Thr Tyr Gly Pro Gly Leu Val Gly Ala Leu Leu Val Gly Leu Ser
                 85                  90                  95

GCT GCC AAG GCC TTT GCT TGG GCT CAC GGA CTT CCA CTG ATT CCT GTT       336
Ala Ala Lys Ala Phe Ala Trp Ala His Gly Leu Pro Leu Ile Pro Val
            100                 105                 110

AAT CAC ATG GCT GGG CAC CTC ATG GCA GCT CAG AGT GTG GAG CCT TTG       384
Asn His Met Ala Gly His Leu Met Ala Ala Gln Ser Val Glu Pro Leu
        115                 120                 125

GAG TTT CCC TTG CTA GCC CTT TTA GTC AGT GGT GGG CAC ACA GAG TTG       432
Glu Phe Pro Leu Leu Ala Leu Leu Val Ser Gly Gly His Thr Glu Leu
130                 135                 140

GTC TAT GTT TCT GAG GCT GGC GAT TAC AAG ATT GTT GGG GAG ACA CGA       480
Val Tyr Val Ser Glu Ala Gly Asp Tyr Lys Ile Val Gly Glu Thr Arg
145                 150                 155                 160

GAC GAT GCA GTT GGG GAG GCT TAT GAC AAG GTC GGT CGT GTC ATG GGC       528
Asp Asp Ala Val Gly Glu Ala Tyr Asp Lys Val Gly Arg Val Met Gly
                165                 170                 175

TTG ACC TAT CCT GCA GGT CGT GAG ATT GAC GAG CTG GCT CAT CAG GGG       576
Leu Thr Tyr Pro Ala Gly Arg Glu Ile Asp Glu Leu Ala His Gln Gly
            180                 185                 190

CAC GAT ATT TAT GAT TTC CCC CGT GCC ATG ATT AAG GAA GAT AAT CTG       624
His Asp Ile Tyr Asp Phe Pro Arg Ala Met Ile Lys Glu Asp Asn Leu
        195                 200                 205

GAG TTC TCC TTC TCA GGT TTG AAA TCT GCC TTT ATC AAT CTT CAT CAC       672
Glu Phe Ser Phe Ser Gly Leu Lys Ser Ala Phe Ile Asn Leu His His
    210                 215                 220

AAT GCC GAG CAA AAG GGA GAA AGC CTG TCT ACA GAA GAT TTG TGT GCT       720
Asn Ala Glu Gln Lys Gly Glu Ser Leu Ser Thr Glu Asp Leu Cys Ala
225                 230                 235                 240

TCC TTC CAA GCA GCA GTT ATG GAC ATT CTC ATG GCA AAA ACC AAG AAG       768
Ser Phe Gln Ala Ala Val Met Asp Ile Leu Met Ala Lys Thr Lys Lys
                245                 250                 255

GCT TTG GAG AAA TAT CCT GTT AAA ACC CTA GTT GTG GCA GGT GGT GTG       816
Ala Leu Glu Lys Tyr Pro Val Lys Thr Leu Val Val Ala Gly Gly Val
            260                 265                 270
```

-continued

```
GCA GCC AAT AAA GGT CTC AGA GAA CGC CTA GCA ACT GAA ATC ACA GAT      864
Ala Ala Asn Lys Gly Leu Arg Glu Arg Leu Ala Thr Glu Ile Thr Asp
            275                 280                 285

GTC AAT GTT ATC ATT CCA CCT CTG CGT CTC TGC GGA GAC AAT GCA GGT      912
Val Asn Val Ile Ile Pro Pro Leu Arg Leu Cys Gly Asp Asn Ala Gly
        290                 295                 300

ATG ATT GCT TAT GCC AGT GTC AGC GAG TGG AAC AAA GAA AAC TTT GCA      960
Met Ile Ala Tyr Ala Ser Val Ser Glu Trp Asn Lys Glu Asn Phe Ala
305                 310                 315                 320

AAC TTG GAC CTC AAT GCC AAA CCA AGT CTT GCC TTT GAT ACC ATG GAA     1008
Asn Leu Asp Leu Asn Ala Lys Pro Ser Leu Ala Phe Asp Thr Met Glu
                325                 330                 335

TAA                                                                  1011
```

(2) INFORMATION FOR SEQ ID NO:4:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Asp Arg Tyr Ile Leu Ala Phe Glu Thr Ser Cys Asp Glu Thr
1               5                   10                  15

Ser Val Ala Val Leu Lys Asn Asp Asp Glu Leu Leu Ser Asn Val Ile
                20                  25                  30

Ala Ser Gln Ile Glu Ser His Lys Arg Phe Gly Gly Val Val Pro Glu
            35                  40                  45

Val Ala Ser Arg His His Val Glu Val Ile Thr Ala Cys Ile Glu Glu
        50                  55                  60

Ala Leu Ala Glu Ala Gly Ile Thr Glu Glu Asp Val Thr Ala Val Ala
65                  70                  75                  80

Val Thr Tyr Gly Pro Gly Leu Val Gly Ala Leu Leu Val Gly Leu Ser
                85                  90                  95

Ala Ala Lys Ala Phe Ala Trp Ala His Gly Leu Pro Leu Ile Pro Val
            100                 105                 110

Asn His Met Ala Gly His Leu Met Ala Ala Gln Ser Val Glu Pro Leu
        115                 120                 125

Glu Phe Pro Leu Leu Ala Leu Leu Val Ser Gly Gly His Thr Glu Leu
    130                 135                 140

Val Tyr Val Ser Glu Ala Gly Asp Tyr Lys Ile Val Gly Glu Thr Arg
145                 150                 155                 160

Asp Asp Ala Val Gly Glu Ala Tyr Asp Lys Val Gly Arg Val Met Gly
                165                 170                 175

Leu Thr Tyr Pro Ala Gly Arg Glu Ile Asp Glu Leu Ala His Gln Gly
            180                 185                 190

His Asp Ile Tyr Asp Phe Pro Arg Ala Met Ile Lys Glu Asp Asn Leu
        195                 200                 205

Glu Phe Ser Phe Ser Gly Leu Lys Ser Ala Phe Ile Asn Leu His His
    210                 215                 220

Asn Ala Glu Gln Lys Gly Glu Ser Leu Ser Thr Glu Asp Leu Cys Ala
225                 230                 235                 240

Ser Phe Gln Ala Ala Val Met Asp Ile Leu Met Ala Lys Thr Lys Lys
                245                 250                 255
```

-continued

```
Ala Leu Glu Lys Tyr Pro Val Lys Thr Leu Val Val Ala Gly Gly Val
            260                 265                 270

Ala Ala Asn Lys Gly Leu Arg Glu Arg Leu Ala Thr Glu Ile Thr Asp
        275                 280                 285

Val Asn Val Ile Ile Pro Pro Leu Arg Leu Cys Gly Asp Asn Ala Gly
    290                 295                 300

Met Ile Ala Tyr Ala Ser Val Ser Glu Trp Asn Lys Glu Asn Phe Ala
305                 310                 315                 320

Asn Leu Asp Leu Asn Ala Lys Pro Ser Leu Ala Phe Asp Thr Met Glu
                325                 330                 335
```

(2) INFORMATION FOR SEQ ID NO:5:

(i) SEQUENCE CHARACTERISTICS:
        (A) LENGTH: 1008 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:5:

```
AUGAAGGAUA GAUAUAUUUU AGCAUUUGAG ACAUCCUGUG AUGAGACCAG UGUCGCCGUC      60

UUGAAAAACG ACGAUGAGCU CUUGUCCAAU GUCAUUGCUA GUCAAAUUGA GAGUCACAAA     120

CGUUUUGGUG GCGUAGUGCC CGAAGUAGCC AGUCGUCACC AUGUCGAGGU CAUUACAGCC     180

UGUAUCGAGG AGGCAUUGGC AGAAGCAGGG AUUACCGAAG AGGACGUGAC AGCUGUUGCG     240

GUUACCUACG GACCAGGCUU GGUCGGAGCC UUGCUAGUUG GUUUGUCAGC UGCCAAGGCC     300

UUUGCUUGGG CUCACGGACU UCCACUGAUU CCUGUUAAUC ACAUGGCUGG GCACCUCAUG     360

GCAGCUCAGA GUGUGGAGCC UUUGGAGUUU CCCUUGCUAG CCCUUUUAGU CAGUGGUGGG     420

CACACAGAGU UGGUCUAUGU UUCUGAGGCU GGCGAUUACA AGAUUGUUGG GGAGACACGA     480

GACGAUGCAG UUGGGGAGGC UUAUGACAAG GUCGGUCGUG UCAUGGGCUU GACCUAUCCU     540

GCAGGUCGUG AGAUUGACGA GCUGGCUCAU CAGGGGCACG AUAUUUAUGA UUUCCCCCGU     600

GCCAUGAUUA AGGAAGAUAA UCUGGAGUUC UCCUUCUCAG GUUUGAAAUC UGCCUUUAUC     660

AAUCUUCAUC ACAAUGCCGA GCAAAAGGGA GAAAGCCUGU CUACAGAAGA UUUGUGUGCU     720

UCCUUCCAAG CAGCAGUUAU GGACAUUCUC AUGGCAAAAA CCAAGAAGGC UUUGGAGAAA     780

UAUCCUGUUA AAACCCUAGU UGUGGCAGGU GGUGUGGCAG CCAAUAAAGG UCUCAGAGAA     840

CGCCUAGCAA CUGAAAUCAC AGAUGUCAAU GUUAUCAUUC CACCUCUGCG UCUCUGCGGA     900

GACAAUGCAG GUAUGAUUGC UUAUGCCAGU GUCAGCGAGU GGAACAAAGA AAACUUUGCA     960

AACUUGGACC UCAAUGCCAA ACCAAGUCUU GCCUUUGAUA CCAUGGAA               1008
```

STREPTOCOCCUS PNEUMONIAE GENE SEQUENCE GCP

BACKGROUND OF THE INVENTION

This application claims the benefit of U.S. Provisional application No. 60/036,281, filed Dec. 13, 1996.

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae*.

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding a protein (viz. Gcp) that is essential for viability.

In another embodiment, the invention relates to a nucleic acid molecule comprising the nucleotide sequences identified as SEQ ID NO:1, SEQ ID NO:2, SEQ ID NO:3, or SEQ ID NO:5.

In another embodiment, the present invention relates to a nucleic acid that encodes SEQ ID NO:4.

In another embodiment the present invention relates to an isolated protein molecule, wherein said protein molecule comprises the sequence identified as SEQ ID NO:4.

In yet another embodiment, the present invention relates to a recombinant DNA vector that incorporates the gcp gene in operable linkage to gene expression sequences enabling the gene to be transcribed and translated in a host cell.

In still another embodiment the present invention relates to host cells that have been transformed or transfected with the cloned gcp gene such that the gcp gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the gcp protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5× SSPE and 50% formamide, and washing at 50° C. to 65° C. in 0.5× SSPE; typical low stringency conditions comprise hybridizing at 35° C. to 37° C. in 5× SSPE and 40% to 45% formamide and washing at 42° C. in 1×–2× SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of NaH2PO4.H2O, and 7.4 g of EDTA in 800 ml of H2O. The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of H2O. The volume is brought to 1 liter after adjusting the pH with 10N NaOH.

DETAILED DESCRIPTION OF THE INVENTION

The gcp gene disclosed herein (SEQ ID NO:3) and related nucleic acids (for example, SEQ ID NO:1, SEQ ID NO:2 and SEQ ID NO:5) encode an essential protein that is located on the exterior of the cell. Disruption of the native chromosomal sequence encoding gcp, for example, by knockout mutation, results in nonviability. Therefore, gcp can be used to screen for agents that bind or otherwise interact with said protein. Such agents could identify new antibacterial agents.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Production of Knockout Mutations

The invention further provides a method for producing knockout mutations in the *S. pneumoniae* genome corresponding to any region of DNA disclosed herein. Knockout mutations are useful for a variety of applications. For example, the knockout procedure disclosed herein provides a method for (1) identifying the function of a protein in the cell, (2) constructing merodiploid strains, (3) introduction of foreign genes onto the *S. pneumoniae* chromosome, (4) construction of strains with altered regulatory properties, (5) construction of defined mutations in which the genomic sequence is replaced by a specifically mutated copy of the wild-type sequence. Preferred targets for knockout mutation comprise the ORFs disclosed herein (See Tables, Appendix).

Abrogating normal production of a protein is a means of perturbing the cell in a defined way. Critical biological functions can be affected by knockout mutations, and in some instances these can be determined easily by, for example, loss of viability. In other instances the phenotypic affect of a knockout mutation will require systematic screens to test for losses in specific enzyme activities or, for changes in growth requirements, for example.

In one embodiment "knockout mutation cassettes" are created by interrupting a natural DNA sequence with a foreign piece of DNA and replacing the wild-type chromosomal copy of the sequence with the knockout cassette (See FIG. 2). In this embodiment, the knockout protocol involves cloning a foreign piece of DNA into the target DNA such that "tails" comprising the target site DNA remain at the 5' and 3' ends of the knockout cassette. The size of tails flanking the cassette should be at least 50 base pairs and preferably greater than 200 to 500 base pairs for efficient recombination and/or gene conversion. For convenience at a later selection step, the foreign DNA cloned into the target DNA also provides a selectable marker, for example, an antibiotic resistance gene.

The knockout procedure can be carried out by mixing a knockout gene cassette with a culture of *S. pneumoniae* competent for DNA uptake. While *S. pneumoniae* is naturally transformable it is preferred that cells be rendered competent for DNA uptake by any suitable method (See e.g. LeBlanc et.al. Plasmid 28, 130–145, 1992; Pozzi et al. J. Bacteriol.178, 6087–6090, 1996). Where the target DNA is disrupted with an antibiotic resistance gene, selection of transformants is carried out on agar plates containing suitable levels of an appropriate antibiotic. Following transformation, a fraction of cells that have taken up the knockout cassette will have undergone homologous recombination or gene conversion across the genomic DNA tails of the cassette, resulting in replacement of the wild-type genomic sequence with the knockout cassette (See FIG. 2). Knockout recombination events are easily confirmed by, for example, Southern blot hybridization, or more conveniently by PCR.

In the preferred method for producing knockout mutations in S. pneumoniae, a fragment of S. pneumoniae genomic DNA (i.e. target site) disclosed herein is cloned into a suitable plasmid or other vector. The recombinant vector is introduced into E. coli by transformation and transferred from E. coli to S. pneumoniae by conjugation. The knockout vector then recombines with the S. pneumoniae chromosome across the target site to produce a disrupted genomic fragment (See FIG. 1). The target DNA can comprise any DNA sequence disclosed herein, and is easily made by the PCR using conventional techniques. A suitable cloning vector for the conjugation method has several salient features. First, the vector should replicate and be selectable in E. coli, (2) the vector should be selectable but not replicate in S. pheumoniae, and (3) the vector should be transferable from E. coli to S. pheumoniae by conjugation. A preferred cloning vector for this purpose is pCZA342 (See FIG. 3). The conjugation method of the knockout procedure is disclosed more fully in the accompanying Examples.

Skilled artisans will recognize that the DNA molecules of this invention, or fragments thereof, can be generated by general cloning methods. PCR amplification using oligonucleotide primers targeted to any suitable region of SEQ ID NO:3 is preferred. Methods for PCR amplification are widely known in the art. See e.g. PCR Protocols: A Guide to Method and Application, Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, Methods in Enzymology, 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., Oligonucleotide Synthesis, A Practical Approach, (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, Bioorganic Chemistry (1981) Springer-Verlag, N.Y., 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the Escherichia coli K12 strain 294 (ATCC No. 31446) is particularly useful for expression of foreign proteins. Other strains of E. coli, bacilli such as Bacillus subtilis, enterobacteriaceae such as Salmonella typhimurium or Serratia marcescans, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast Saccharomyces cerevisiae is commonly used. Other yeasts, such as Kluyveromyces lactis, are also suitable. For expression of recombinant genes in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene, a selectable marker for a trp1 mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to Streptococcus pneumoniae DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In Methods in Enzymology, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of *E. coli* that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;

b) exposing the protein or membranes to a test compound; and c) detecting an interaction of a protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. The reaction/interaction of said protein and said compound is monitored by any suitable means. In a preferred method, a radioactively-labeled or chemically-labeled compound or protein is used. A specific association between the test compound and protein is monitored by any suitable means.

In such a screening protocol HPLFP is prepared as described herein, preferably using recombinant DNA technology. A test compound is introduced into a reaction vessel containing the HPLFP protein or fragment thereof. Binding of HPLFP by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a HPLFP protein, perhaps as a lead to a pharmaceutical compound for modulating the state of differentiation of an appropriate tissue. A ligand that binds HPLFP, or related fragment thereof, is identified, for example, by combining a test ligand with HPLFP under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing S. pheumoniae gcp Gene in a Host Cell

An expression vector suitable for expressing S. pneumoniae gcp in a variety of procaryotic host cells, such as E. coli, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the gcp coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the S. pheumoniae gcp (SEQ ID NO:1). The coding region for gcp is easily produced by PCR technology using suitably designed primers to the ends of the coding region specified in SEQ ID NO:1.

The gcp used in this construction is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

Example 2

Recombinant Expression and Purification of a Protein Encoded by S. pheumoniae gcp An expression vector that carries gcp from the S. pneumoniae genome as disclosed herein and which gcp is operably-linked to an expression promoter is transformed into E. coli BL21 (DE3)(hsdS gal lcIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product. After removing unbound proteins and other materials by washing the column with any suitable buffer, pH 7.5, the bound protein is eluted in any suitable buffer at pH 4.3, or preferably with an imidizole-containing buffer at pH 7.5.

---

We claim:

1. An isolated polynucleotide, wherein said polynucleotide has a sequence selected from the group consisting of:

(a) SEQ ID NO:3;

(b) SEQ ID NO:5 and (c) a polynucleotide complementary to (a) or (b).

2. An isolated polynucleotide, wherein said polynucleotide has a sequence selected from the group consisting of:

(a) SEQ ID NO:2; and (b) SEQ ID NO:2.

3. An isolated polynucleotide of claim 1 wherein the sequence of said polynucleotide is SEQ ID NO:3 or a sequence complementary to SEQ ID NO:3.

4. An isolated polynucleotide of claim 1 wherein the sequence of said polynucleotide is SEQ ID NO:5 or a sequence complementary to SEQ ID NO:5.

5. A vector comprising an isolated polynucleotide of claim 1.

6. A vector, as in claim 5, wherein said isolated polynucleotide is SEQ ID NO:3, operably-linked to a promoter sequence.

7. A host cell containing a vector of claim 5.

8. A host cell containing a vector of claim 4.

9. A method for constructing a recombinant host cell having the potential to express SEQ ID NO:4, said method comprising introducing into said host cell by any suitable means a vector of claim 6.

10. A method for expressing SEQ ID NO:4 in a recombinant host cell of claim 8, said method comprising culturing said recombinant host cell under conditions suitable for gene expression.

* * * * *